United States Patent [19]

De Smet

[11] Patent Number: 4,956,285
[45] Date of Patent: Sep. 11, 1990

[54] PROCESS FOR THE PREPARATION OF S-2,2-R₁,R₂-1,3-DIOXOLANE-4-METHANOLS

[75] Inventor: Marie-José De Smet, Zeist, Netherlands

[73] Assignee: Gist-Brocades N.V., Delft, Netherlands

[21] Appl. No.: 396,927

[22] Filed: Aug. 18, 1989

[30] Foreign Application Priority Data

Jun. 29, 1989 [EP] European Pat. Off. ........ 89201733.6

[51] Int. Cl.⁵ .................. C12P 17/04; C12P 1/04; C07P 41/00
[52] U.S. Cl. .................................. 435/126; 435/170; 435/171; 435/176; 435/177; 435/280; 435/822; 435/911; 435/912
[58] Field of Search ............... 435/126, 170, 171, 176, 435/177, 911, 912, 280, 822

[56] References Cited

U.S. PATENT DOCUMENTS 4,575,558 3/1986 Mai et al. .................. 549/453

OTHER PUBLICATIONS

Chem Abs. CA01-23377(3), CMLTAG (3), pp. 401–404, 1984, Mukaiyama et al., Chem. Lett.
Biochem Abs. 89-12188, Terao et al., CPBTAL, Chem. Pharm. Bull. (1989), 37, 6, 1653-55.
Biochem. Abs. 88-02888 (EP-244912), Nov. 11, 1987.
Derwent Abs. 89-132554/18, Vbe Ind, J01075435 (Mar. 1989).
Derwent Abs. 87-315098/45, Bertola et al., EP-244912 (Nov. 1987).

*Primary Examiner*—Herbert J. Lilling
*Attorney, Agent, or Firm*—Bierman and Muserlian

[57] ABSTRACT

A process for the preparation of an enriched S-isomer of a 2,2-R₁,R₂-1,3-dioxolane-4-methanol of the formula

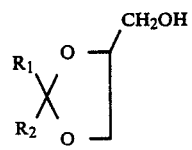

wherein $R_1$ and $R_2$ are individually selected from the group consisting of hydrogen and alkyl of 1 to 6 carbon atoms or taken together with the carbon atom to which they are attached form a carbocyclic ring of 3 to 6 carbon atoms comprising subjecting a mixture of R and S isomers of formula I to the action of a microorganism or a substance derived therefrom capable of stereoselective consumption of the R form of formula I for a period of time sufficient to consume the R-isomer to obtain an enriched S isomer of the compound of formula I. Preferably, at least 50% by weight of the R-isomer is consumed.

The present invention relates to a process for the preparation of 2,2-$R_1$,$R_2$,-1,3-dioxolane-4-methanol consisting predominantly of or substantially completely of S-isomer.

12 Claims, No Drawings

PROCESS FOR THE PREPARATION OF S-2,2-$R_1$,$R_2$-1,3-DIOXOLANE-4-METHANOLS

STATE OF THE ART

S-2,2-$R_1$,$R_2$-1,3-dioxolane-4-methanols are an important starting material for the preparation of agricultural and pharmaceutical products, see for example Jurczak et al., Tetrahedron, Vol. 42, No. 2, pp. 447 to 488 (1986). In recent years, S-2,2-$R_1$,$R_2$-1,3-dioxolane-4-methanols have become of interest as important starting compounds for the preparation of many biologically active products and especially for the preparation of chiral drugs. The preparation of biologically active products in optically pure form using chiral starting materials is very advantageous, enabling precise planning and efficient realization of synthetic pathways. S-2,2-$R_1$,$R_2$-1,3-dioxolane-4-methanols are an important example of $C_3$-synthon and are used as starting compound for the preparation of many other $C_3$-synthons which are widely used in organic synthesis as a chiral building block. For example, S-2,2-$R_1$,$R_2$-1,3-dioxolane-4-methanols can be used in the synthesis of other chiral synthons, monosaccharides, their derivatives and other polyhydroxyl systems, and biologically active products of more complex structure.

OBJECTS OF THE INVENTION

It is an object of the invention to provide an industrial economical process for the stereoselective preparation of the S-isomers of 2,2-$R_1$,$R_2$-1,3-dioxolane-4-methanols of formula I.

This and other objects and advantages of the invention will become obvious from the following detailed description.

THE INVENTION

The novel process of the invention for the preparation of an enriched S-isomer of a 2,2-$R_1$,$R_2$-1,3-dioxolane-4-methanol of the formula

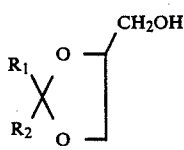

wherein $R_1$ and $R_2$ are individually selected from the group consisting of hydrogen and alkyl of 1 to 6 carbon atoms or taken together with the carbon atom to which they are attached form a carbocyclic ring of 3 to 6 carbon atoms comprises subjecting a mixture of R and S isomers of formula I to the action of a microorganism or a substance derived therefrom capable of stereoselective consumption of the R form of formula I for a period of time sufficient to consume the R-isomer to obtain an enriched S isomer of the compound of formula I. Moreover, it has been found that the R-stereoisomer of 2,2-$R_1$,$R_2$-1,3-dioxolane-4-methanol may be advantageously converted into S-2,2-$R_1$,$R_2$-1,3-dioxolane-4-carboxylic acid using these microorganisms or substances derived therefrom.

European Patent Application EP-A-0244912 describes a process for the preparation of the R-isomer of 2,2-$R_1$,$R_2$-1,3-dioxolane-4-methanol starting with the racemate wherein the S-isomer is oxidized to its corresponding acid. The enzyme system(s) involved in the oxidation of (R) isomer is (are) a completely different enzyme system(s) than the one(s) involved in the oxidation of (S) isomer. In general, the (R) and (S) enantiomer of a compound behave as two different substrates in enzymatic conversions.

The present invention provides a process for the preparation of 2,2-$R_1$,$R_2$-1,3-dioxolane-4-methanol enriched in S-isomer wherein $R_1$ and $R_2$ are hydrogen or alkyl groups, optionally substituted or branched, or wherein $R_1$ and $R_2$ together with the carbon atom to which they are attached form a carbocyclic ring, optionally substituted, which comprises subjecting a mixture of R- and S-2,2-$R_1$,$R_2$-1,3-dioxolane-4-methanol to the action of a microorganism or substances derived therefrom having the ability for stereoselective consumption of R-2,2-$R_1$,$R_2$-1,3-dioxolane-4-methanol for a period of time such that R-2,2-$R_1$,$R_2$-1,3-dioxolane-4-methanol in the mixture is consumed to give a 2,2-$R_1$,$R_2$-1,3-dioxolane-4-methanol enriched in S-isomer. Preferably at least 50 wt % of R-2,2-$R_1$,$R_2$-1,3-dioxolane-4-methanol is consumed to give 2,2-$R_1$,$R_2$-1,3-dioxolane-4-methanol enriched in S-isomer or consisting of substantially pure S-isomer. The 2,2-$R_1$,$R_2$-1,3-dioxolane-4-methanol enriched in S-isomer is at least partly isolated and/or used as starting material for the preparation of other optically active compounds.

Advantageously, $R_1$ and $R_2$ are alkyl of less than 6 carbon atoms or wherein the carbocyclic ring contains less than 8 carbon atoms. Preferably, $R_1$ and $R_2$ are identical since in this way, no extra asymmetry is introduced into the compounds. More preferably, $R_1$ and $R_2$ are alkyl of 1 to 3 carbon atoms or together with the carbon atom to which they are attached form a carbocyclic ring of 5 or 6 carbon atoms.

As hereinbefore described, the mixture of R and S isomers of the 2,2-$R_1$,$R_2$-1,3-dioxolane-4-methanols may be converted into 2,2-$R_1$,$R_2$-1,3-dioxolane-4-methanols enriched in the S-isomer. In this way, only part of the mixture can be used in further reactions, for example starting with a 50 wt % R and 50 wt % S-mixture, only half of the 2,2-$R_1$,$R_2$-1,3-dioxolane-4-methanol becomes available in a useful way. According to an embodiment of the invention, the R-2,2-$R_1$,$R_2$-1,3-dioxolane-4-methanol is advantageously converted into S-2,2-$R_1$,$R_2$-1,3-dioxolane-4-carboxylic acid.

In this way, not only is the preparation of 2,2-$R_1$,$R_2$-1,3-dioxolane-4-methanols enriched in S-isomer possible, but at the same time 2,2-$R_1$,$R_2$-1,3-dioxolane-4-carboxylic acids enriched in S-isomer may be obtained. In this way, substantially the R as well as the S-2,2-$R_1$,$R_2$-1,3-dioxolane-4-ethanol may be used. The 2,2-$R_1$,$R_2$-1,3-dioxolane-4-carboxylic acid enriched in S-isomer may be used as the starting compound for the preparation of many biologically active products or may be converted to the 2,2-$R_1$,$R_2$-1,3-dioxolane-4-methanol enriched in R-isomer, which is an important starting compound as well.

By the term "microorganisms having the ability for stereoselective consumption" is meant, for example, bacteria, yeasts and fungi. Preferably, yeasts and fungi are used and more preferably microorganisms belonging to the genus Absidia, to the genus Branhamella or to the gnus Graphium are used. Also microorganisms, which have obtained the ability for consumption of R-2,2-$R_1$,$R_2$-1,3-dioxolane-4-methanol through the introduction of novel genetic material are embodied by the term "microorganism having the ability for stereoselective consumption".

The latter can be accomplished by transferring the cloned gene encoding a polypeptide responsible for the steresoselective consumption, an enzyme from any of the screened microorganisms to another microorganism, particularly to *Escherichia coli*. Other microorganism may be belonging to the genus Saccharomyces, Kluyveromyces, Bacillus, Nocardia, Rhodococcus, Escherichia and Corynebacterium. Cloned genes may be selected for their ability to encode an enzyme capable of consuming of R-2,2-$R_1$,$R_2$-1,3-dioxolane-4-methanol, preferably S-2,2-dimethyl-1,3-dioxolane-4-methanol. Alternatively, they may be selected by cross-hybridization with an already selected gene encoding an enzyme for the stereoselective consumption.

The microorganisms may advantageously be immobilized, for example, on a polymer gel. This can be done with growing cells, non-growing cells and/or killed cells, but alternatively with suitable enzymes derived therefrom which may be purified to a certain extent if a higher specific activity is needed.

Therefore, the term "microorganisms or substances derived therefrom" means the microorganisms in a growing stage, in a nongrowing stage or killed, extracts therefrom, optionally concentrated or purified. For example, enzymes optionally in combination with for example, artifical or natural co-factors, may be used. No fermentatively active cells may be used for the consumption of the R-2,2-$R_1$,$R_2$-1,3-dioxolane-4-methanol.

It is found that enzymes derived from the cells or killed cells may consume the R-isomer under suitable conditions. The microorganisms or substances derived therefrom may be used several times and are active for at least 2 weeks. Even without co-substrate (for example glucose), the microorganisms may remain active. The enrichment in S-isomer of 2,2-$R_1$,$R_2$-1,3-dioxolane-4-methanol may take place in suitable buffers (for example 3-(N-morpholino)-propane sulfonic acid, tris(hydroxymethyl)aminomethane or potassium phosphate) as well as in physiological salts. After being stored, the induced cells are found to be directly capable to transform the enrichment in S-isomer.

More particularly, the microorganism for the consumption of R-2,2-$R_1$,$R_2$-1,3-dioxolane-4-methanols include cultures of *Absiia glauca* (a sample of this species is deposited with the CBS under the accession number of 306.89), *Branhamella catarrhalis* (a sample of this species is deposited with the CBS under the accession number of 307.89) and *Graphium penicillioides* (a sample of this species is deposited with the CBS under the accession number of 318.72). CBS is Centraal Bureau voor Schimmelcultures, Oosterstraat 1, 3740 AG Baarn, The Netherlands.

The S-2,2-$R_1$,$R_2$-1,3-dioxolane-4-methanol produced by the present invention may be used as a starting material for the production of other optically active compounds and an important use is in the production of chiral drugs.

It will be appreciated by everyone skilled in the art that any suitable process may be used to convert S and R-2,2-$R_1$,$R_2$-1,3-dioxolane-4-methanol into the optically active compounds.

Examples which illustrate the use of S and R-2,2-$R_1$,$R_2$-1,3-dioxolane-4-methanol for the preparation of optically active compounds are known from, for example, Jurczak et al, Tetrahedron report number 195, Tetrahedron, Vol. 42 (1986), p. 447 to 488 and the Technical Information Bulletin 225, Sep. 1983 of Janssen Chimica (Belgium). The optically active compounds may be used in pharmaceutical or agricultural products.

According to a preferred embodiment of the process of the invention, a microorganism having the ability for stereoselective consumption of R-2,2-$R_1$,$R_2$-1,3-dioxolane-4-methanols is cultured for about 0.5 to 10 days, whereafter the cells of the microorganisms are suspended in a liquid nutrient medium and the mixture of R- and S-2,2-$R_1$,$R_2$-1,3-dioxolane-4-methanol is subjected to the action of the cells. After the abovementioned cultivation for about 0.5 to 10 days, the cells may be isolated from the culturing medium before suspending the cells in the liquid nutrient medium.

To grow the microorganism used for the selective consumption of S-2,2-$R_1$,$R_2$-1,3-dioxolane-4-methanols, ordinary culture mediums containing an assimilable carbon source (for example glucose, lactate, sucrose, etc.), an assimilable nitrogen source (for example ammonium sulfate, ammonium nitrate, ammonium chloride, etc.), with an agent for an organic nutrient source (for example yeast extract, malt extract, peptone, meat extract, etc.) and an inorganic nutrient source (for example phosphate, magnesium, potassium, zinc, iron and other metals in trace amounts) may be used.

Another preferred culture medium is a YPD-medium optionally enriched with one or more ingredients. Such a YPD-medium consisting of 20 g/l of Bactopeptone (TM), 10 g/l of yeast extract and 20 g/l of glucose may be used. Before use, the medium is conveniently sterilized for 30 minutes at 110° C. Another preferred culture medium is a skimmed milk medium optionally enriched with one or more ingredients, for example, a skimmed milk medium containing 10% of skimmed milk from skimmed milk powder which is conveniently sterilized for 30 minutes at 110° C. before use. Examples of enrichments to the skimmed milk medium include Maxatase (TM) (Gist-Brocades).

A temperature of 0° to 45° C. and a pH of 3.5 to 9 is preferably maintained during the growth of the microorganism. Preferably, the microorganism is grown at a temperature of 20° to 37° C. and at a pH of 5 to 9. The aerobic conditions required during the growth of the microorganims can be provided by any of the well-established procedures, provided that the supply of oxygen is sufficient to meet the metabolic requirement of the microorganism. This is most conveniently achieved by supplying oxygen, suitably in the form of air, and optionally at the same time shaking or stirring the reaction liquid. During the consumption of R-2,2-$R_1$,$R_2$-1,3-dioxolane-4-methanols by the microorganism, the microorganism might be in a growing stage using an abovementioned ordinary culture medium.

During the consumption of R-2,2-$R_1$,$R_2$-1,3-dioxolane-4-methanols by the microorganism, an ordinary culture medium may be used containing an assimilable carbon source when required (for example glucose, lactate, sucrose, etc.), an assimilable nitrogen source when required (for example ammonium sulfate, ammonium nitrate, ammonium chloride, etc.), with an organic nutrient source when required (for example yeast extract, malt extract, peptone, meat extract, etc.) and an inorganic nutrient source when required (for example phosphate, magnesium, potassiu, zinc, iron and other metals in trace amounts. Advantageously, during the enrichment of S-isomer, a YPD-medium or a skimmed milk medium (as described above) optionally enriched with one or more ingredients can be used.

The microorganism can be kept in the non-growing stage, for example, by exclusion of the assimilable carbon source or by exclusion of the nitrogen source. A temperature of 0° to 45° C. and a pH of 3.5 to 9 can be maintained during this stage.

Preferably, the microorganisms are kept at a temperature of 20° to 37° C. and a pH of 5 to 9. The aerobic conditions required during this stage can be provided by any of the well-established procedures, provided that the supply of oxygen is sufficient to meet the metabolic requirement of the microorganisms. This is most conveniently achieved by supplying oxygen, suitably in the form of air and optionally, at the same time, shaking or stirring the reaction liquid. The S- and any remaining R-2,2-$R_1$,$R_2$-1,3-dioxolane-4-methanol after transformation as mentioned above, can then be recovered and purified according to any of the procedures known per se for such products.

The microorganisms can be kept on agar slants, frozen in 50% glycerol or lyophilized. If required, precultures of these microorganisms can be made by any of the well-established procedures, for example, the microorganisms can be incubated in bouillon or in BHI (Brain Heart Infusion) for 24 hours at 30° C. in a rotary shaker. A bouillon medium of the following composition can be used: Lab Lemco L 29 (meat extract, Oxoid (TM) (9 g/l), Bactopeptone (TM) (10 g/l) and sodium chloride (5 g/l), the pH being adjusted to 7.6. Before use, this medium is conveniently sterilized for 20 minutes at 120° C. A BHI medium containing 0.037 g/l (BHI (Oxoid (TM)), the pH adjusted to 7.0, can be used. Before use, this medium is conveniently sterilized for 20 minutes at 120° C.

In the following examples there are described several preferred embodiments to illustrate the invention. However, it should be understood that the invention is not intended to be limited to the specific embodiments.

EXAMPLES 1 to 3

The microorganisms of Table I (yeasts and other fungi) were grown for 24 to 48 hours at 26° C. in 125 ml baffled flasks containing 25 m of YPD medium After this period, the cell mass was collected by centrifugation and resuspended in 25 ml of 10% hydrolyzed skim milk medium [Hydrolyzed skim milk medium: 100 g/l of skim milk powder (Oxoid) was adjusted to a pH of 7.8 and 25 ml of a filtered solution of 40 g/l Maxatase (TM) were added; the final solution was stirred at 40° C. for one hour and adjusted to a pH of 7.0 followed by sterilization for 30 minutes at 110° C.]. About 2.5 g/l of R,S 2,2-dimethyl-1,3-dioxolane-4-methanol were added and the mixtures were shaken in 125 ml baffled flasks at 26° C. for 48 hours. The mixtures were extracted with 25 ml of ethyl acetate to recover about 40% by weight of the 2,2-$R_1$,$R_2$-1,3-dioxolane-4-methanol. Then, one culture of each form was taken, extracted and the remaining 2,2-$R_1$,$R_2$-1,3-dioxolane-4-methanol was analyzed. The enantiomeric distribution was determined by formation of diastereoisomers with N,O-bis-(trimethylsilyl)-trifluoracetamide (BSTFA) which were separated on a chiral complexation column. The results are given in Table 1.

TABLE 1

| Example | Microorganism | g/l* | enantiomeric rate % R | % S |
|---|---|---|---|---|
| 1 | Absidia glauca (CBS 306.89) | 1.3 | 43 | 57 |

TABLE 1-continued

| Example | Microorganism | g/l* | enantiomeric rate % R | % S |
|---|---|---|---|---|
| 2 | Branhamella Catarrhalis (CBS 307.89) | 1.9 | 33 | 67 |
| 3 | Graphium penicillioides (CBS 318.72) | 1.1 | 29 | 71 |

*The values presented have been corrected for loss due to extraction.

Various modifications of the process of the invention may be made without departing from the spirit or scope thereof and it should be understood that the invention is intended to be limited only as defined in the appended claims.

What is claimed is:

1. A process for the preparation of an enriched S-isomer of a 2,2-$R_1$,$R_2$-1,3-dioxolane-4-methanol of the formula

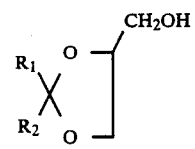

wherein $R_1$ and $R_2$ are individually selected from the group consisting of hydrogen and alkyl of 1 to 6 carbon atoms or taken together with the carbon atom to which they are attached form a carbocyclic ring of 3 to 6 carbon atoms comprising subjecting a mixture of R and S isomers of formula I to the action of a microorganism or an enzyme derived therefrom capable of stereoselective consumption of the R form of formula I for a period of time sufficient to consume the R-isomer to obtain an enriched S isomer of the compound of formula I.

2. The process of claim 1 wherein at least 50% of the R-isomer of formula I in the mixture is consumed.

3. The process of claim 1 wherein $R_1$ and $R_2$ are identical.

4. The process of claim 1 wherein $R_1$ and $R_2$ are hydrogen or alkyl of 1 to 3 carbon atoms.

5. The process of claim 1 wherein $R_1$ and $R_2$ together with the carbon atom to which they are attached form a carbocyclic of 5 to 6 carbon atoms.

6. The process of claim 1 wherein the microorganism is selected from the group consisting of bacterium, yeast and fungi.

7. The process of claim 6 wherein the microorganism belongs to a genus selected from the group consisting of Absidia, Branhamella and Graphium.

8. The process of claim 6 wherein microorganism is selected from the group consisting of *Absidia glauca, Branhamella catarrhalis* and *Graphium penicilliodes.*

9. The process of claim 8 wherein the microorganism is selected from the group consisting of *Absidia glauca* (CBS 306.89), *Branhamella catarrhalis* (CBS 307.89) and *Graphium pencilliodes* (CBS 318.72) and mutants thereof.

10. The process of claim 1 wherein the microorganism or substance desired therefrom is immobilized as a member of the group consisting of growing cell, non-growing cell, a killed cell and an enzyme.

11. The process of claim 1 wherein the R-isomer of formula I is converted into the corresponding S-isomer of 2,2-$R_1$,$R_2$-1,3-dioxolane-4-carboxylic acid.

12. A process for the preparation of a 2,2-$R_1$,$R_2$-1,3-dioxolane-4-methanol enriched in the R- form comprising converting the product of claim 11 into the R-isomer of the compound of formula I.

* * * * *